United States Patent
Chi et al.

(10) Patent No.: US 10,922,513 B2
(45) Date of Patent: Feb. 16, 2021

(54) ELECTRONIC COMPONENT AND ELECTRONIC DEVICE COMPRISING SAME

(71) Applicant: Samsung Electronics Co., Ltd., Suwon-si (KR)

(72) Inventors: Youn-Oh Chi, Suwon-si (KR); Yun-Jang Jin, Yongin-si (KR); Kyung-Hoon Song, Yongin-si (KR); Kwang-Sub Lee, Yongin-si (KR); Se-Young Jang, Seongnam-si (KR); Chi-Hyun Cho, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 170 days.

(21) Appl. No.: 16/327,212

(22) PCT Filed: Jun. 13, 2017

(86) PCT No.: PCT/KR2017/006152
§ 371 (c)(1),
(2) Date: Feb. 21, 2019

(87) PCT Pub. No.: WO2018/043876
PCT Pub. Date: Mar. 8, 2018

(65) Prior Publication Data
US 2019/0188445 A1    Jun. 20, 2019

(30) Foreign Application Priority Data

Aug. 31, 2016  (KR) .................. 10-2016-0111359

(51) Int. Cl.
*G06K 9/00* (2006.01)
*G06F 21/32* (2013.01)
(Continued)

(52) U.S. Cl.
CPC ........ *G06K 9/00013* (2013.01); *A61B 5/1172* (2013.01); *A61B 5/6898* (2013.01);
(Continued)

(58) Field of Classification Search
CPC ..... A61B 5/1172; A61B 5/6898; G06F 21/32; G06F 3/0412; G06K 9/00; G06K 9/00013;
(Continued)

(56) References Cited

U.S. PATENT DOCUMENTS

| 2008/0049980 A1 | 2/2008 | Castaneda et al. |
| 2015/0071509 A1 | 3/2015 | Myers |
| 2015/0245514 A1* | 8/2015 | Choung ............... H05K 5/0247 361/749 |

FOREIGN PATENT DOCUMENTS

| EP | 2 911 169 A2 | 8/2015 |
| JP | 4845090 B2 | 12/2011 |

(Continued)

OTHER PUBLICATIONS

European Search Report dated Aug. 27, 2019, issued in the European Application No. 17846801.3.

*Primary Examiner* — Manuchehr Rahmjoo
(74) *Attorney, Agent, or Firm* — Jefferson IP Law, LLP

(57) ABSTRACT

An electronic component (and/or an electronic device comprising the same) according to various embodiments of the present invention comprises: a substrate having a sensing element mounted on one surface thereof; a flexible printed circuit board that is coupled to the other surface of the substrate so as to face the same and extends to a side of the substrate along a first direction; and at least one recess formed on the edge of the other surface of the substrate, wherein the recess is located in an area, on the other surface of the substrate, which faces at least the flexible printed circuit board, and may extend along a second direction (Continued)

intersecting with the first direction. The electronic component and/or the electronic device comprising the same as described above may be diversified according to embodiments.

15 Claims, 7 Drawing Sheets

(51) Int. Cl.
| | |
|---|---|
| *H04M 1/02* | (2006.01) |
| *H01H 11/04* | (2006.01) |
| *H01H 13/48* | (2006.01) |
| *H01H 11/00* | (2006.01) |
| *H01H 13/84* | (2006.01) |
| *A61B 5/1172* | (2016.01) |
| *A61B 5/00* | (2006.01) |
| *G06F 3/041* | (2006.01) |
| *H01H 13/06* | (2006.01) |
| *H01H 13/14* | (2006.01) |
| *H04M 1/23* | (2006.01) |
| *H01H 3/02* | (2006.01) |

(52) U.S. Cl.
CPC ............ *G06F 3/0412* (2013.01); *G06F 21/32* (2013.01); *G06K 9/00* (2013.01); *H01H 11/00* (2013.01); *H01H 11/04* (2013.01); *H01H 13/06* (2013.01); *H01H 13/14* (2013.01); *H01H 13/48* (2013.01); *H01H 13/84* (2013.01); *H04M 1/02* (2013.01); *H04M 1/23* (2013.01); *H01H 2003/0293* (2013.01); *H01H 2225/002* (2013.01); *H01H 2229/02* (2013.01); *H01H 2229/044* (2013.01); *H01H 2231/022* (2013.01); *H01H 2239/074* (2013.01)

(58) Field of Classification Search
CPC .... G06K 9/00604; G06K 9/209; H01H 11/00; H01H 11/04; H01H 13/06; H01H 13/14; H01H 13/48; H01H 13/84; H01H 2003/0293; H01H 2225/002; H01H 2229/02; H01H 2229/044; H01H 2231/022; H01H 2239/074; H04M 1/02; H04M 1/23
See application file for complete search history.

(56) References Cited

FOREIGN PATENT DOCUMENTS

| | | |
|---|---|---|
| KR | 10-2010-0025860 A | 3/2010 |
| KR | 10-2014-0044061 A | 4/2014 |
| KR | 10-1503183 B1 | 3/2015 |
| KR | 10-2015-0099295 A | 8/2015 |
| KR | 10-1558439 B1 | 10/2015 |

* cited by examiner

ELECTRONIC COMPONENT AND ELECTRONIC DEVICE COMPRISING SAME

CROSS-REFERENCE TO RELATED APPLICATION(S)

This application is a National Phase Entry of PCT International Application No. PCT/KR2017/006152, which was filed on Jun. 13, 2017 and claims priority under 35 U.S.C. § 119 of Korean Patent Application No. 10-2016-0111359, filed on Aug. 31, 2016, in the Korean Intellectual Property Office the disclosure of which is incorporated herein by reference in its entirety.

BACKGROUND

1. Field

Various embodiments of the present disclosure relate to an electronic component. For example, the various embodiments relate to an electronic component that detect various kinds of information (e.g., a fingerprint, an iris, proximity of an object, illuminance, temperature, humidity, etc.) and an electronic device including the electronic component.

2. Description of Related Art

Recently, security-requiring functions such as a mobile banking function, a mobile credit card function, an electronic wallet function, and the like have been installed in portable electronic devices, such as communication terminals. Examples of security functions installed in electronic devices include a user authentication function based on a password or a lock pattern set by a user, and a user authentication function executed via a security company. The authentication method based on a password or executed via a security company may have a low level of security due to a high possibility of leakage of the password, or may be troublesome in that the intervention of the security company is required. As an alternative to this, a biometric authentication method, such as a user authentication method using fingerprint or iris recognition, can provide a simple security function while securing a considerable level of security.

SUMMARY

However, in mounting additional electronic components (e.g., sensor modules) for biometric authentication, it may be difficult to secure a mounting space. For example, it may be difficult to secure a mounting space for an electronic component equipped with an additional fingerprint sensor or iris recognition sensor while reducing the size and weight of an electronic device. In addition, it may be difficult to secure a mounting space for an electronic component equipped with an additional fingerprint sensor or iris recognition sensor while securing a larger screen output region and a larger capacity battery mounting space in a compact and lightweight electronic device (within a limited space of the electronic device).

In some embodiments, an electronic component for a user's biometric authentication may be exposed at least visually out of an electronic device, and thus the electronic component should be compatible with the appearance of the electronic device. Further, when an electronic device is mounted with additional electronic components, a structure may be required that can be easily manufactured and assembled, and can suppress an increase in manufacturing cost.

According to various embodiments, it is possible to provide an electronic component capable of suppressing occurrence of surface imperfections (e.g., a burr) in appearance so as to facilitate assembly with a counterpart component, and an electronic device including the electronic component.

According to various embodiments, it is possible to provide an electronic component, which is easy to process so as to facilitate mass production thereof and to meet the specification of an individual electronic device, and an electronic device including the electronic component.

An electronic component (and/or an electronic device including the electronic component) according to various embodiments of the present disclosure may include: a substrate having a sensor element mounted on one face thereof;
 a flexible printed circuit board coupled to face a remaining face of the substrate and extending to one side of the substrate in a first direction; and
 at least one recess formed at an edge of the remaining face of the substrate,
 in which the recess may be located at least in a region facing the flexible printed circuit board on the remaining face of the substrate, and may extend in a second direction intersecting the first direction.

According to various embodiments, the recess may extend in the second direction across the region facing the flexible printed circuit board. In some embodiments, the second direction may be a direction that is not perpendicular to the first direction, but is inclined at any angle relative to the first direction.

The electronic component according to various embodiments of the present disclosure includes at least one recess formed on one face of the substrate. Thus, the electronic component can be easily processed into a shape suitable for an electronic device. For example, the electronic component itself can be manufactured on the basis of a substrate having a sufficient size, and the substrate can be partially cut using a laser to meet the specifications of the electronic device. Through the cutting using the laser, the substrate can be cut smoothly (or flatly) in the state in which no imperfections (e.g., a burr) are formed. In one embodiment, by forming a recess in the substrate, it is possible to reduce the output of the laser, which is required for cutting the substrate, and through this, it is possible to prevent the flexible printed circuit board from being damaged during the laser cutting process. By making the cut face of the board smoothened while preventing the flexible printed circuit board from being damaged in this way, it is possible to reduce defects in the electronic component and to facilitate the assembly with the electronic device. In some embodiments, a case member may be coupled to the electronic component for exterior decoration, in which the cut face of the substrate is smoothly cut, so that the electronic component can be easily (smoothly) assembled with the case member.

According to various embodiments, each of a plurality of electronic components (e.g., a sensor element, a substrate, and a flexible printed circuit board) may be manufactured in the state of being at least partially buried (e.g., molded) in one molding resin (e.g., a molding portion and/or a molding layer), and may be cut into individual electronic components to match the shape and size required for the electronic device before assembly into the electronic device. For example, electronic components according to various embodiments of the present disclosure can be produced in the state in which a large number of electronic components are initially molded in one molding resin, thereby facilitating mass production. As mentioned above, since the electronic components molded in one molding resin can be separated into individual electronic components by laser cutting, it is possible to easily process and assemble the electronic components to be suitable for individual electronic devices while reducing the manufacturing costs by mass production.

DETAILED DESCRIPTION OF THE DISCLOSURE

Figure 1:
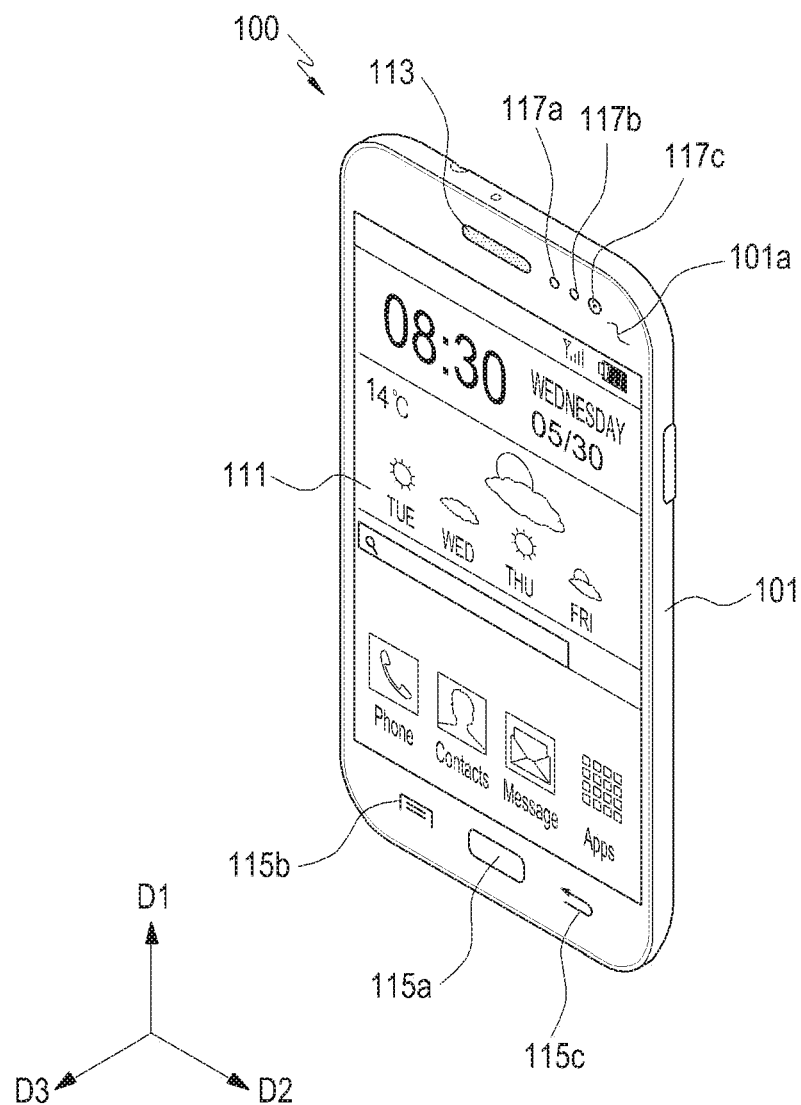
FIG. 1 is a perspective view illustrating an electronic device according to various embodiments of the present disclosure.

As the present disclosure allows for various changes and numerous embodiments, some exemplary embodiments will be described in detail with reference to the accompanying drawings. However, it should be understood that the present disclosure is not limited to the specific embodiments, but the present disclosure includes all modifications, equivalents, and alternatives within the spirit and the scope of the present disclosure.

Although ordinal terms such as "first" and "second" may be used to describe various elements, these elements are not limited by the terms. The terms are used merely for the purpose to distinguish an element from the other elements. For example, a first element could be termed a second element, and similarly, a second element could be also termed a first element without departing from the scope of the present disclosure. As used herein, the term "and/or" includes any and all combinations of one or more associated items.

Further, the relative terms "a front surface", "a rear surface", "a top surface", "a bottom surface", and the like which are described with respect to the orientation in the drawings may be replaced by ordinal numbers such as first and second. In the ordinal numbers such as first and second, their order are determined in the mentioned order or arbitrarily and may not be arbitrarily changed if necessary.

In the present disclosure, the terms are used to describe specific embodiments, and are not intended to limit the present disclosure. As used herein, the singular forms are intended to include the plural forms as well, unless the context clearly indicates otherwise. In the description, it should be understood that the terms "include" or "have" indicate existence of a feature, a number, a step, an operation, a structural element, parts, or a combination thereof, and do not previously exclude the existences or probability of addition of one or more another features, numeral, steps, operations, structural elements, parts, or combinations thereof.

Unless defined differently, all terms used herein, which include technical terminologies or scientific terminologies, have the same meaning as that understood by a person skilled in the art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present specification.

In the present disclosure, an electronic device may be a random device, and the electronic device may be called a terminal, a portable terminal, a mobile terminal, a communication terminal, a portable communication terminal, a portable mobile terminal, a touch screen or the like.

For example, the electronic device may be a smartphone, a portable phone, a game player, a TV, a display unit, a heads-up display unit for a vehicle, a notebook computer, a laptop computer, a tablet Personal Computer (PC), a Personal Media Player (PMP), a Personal Digital Assistants (PDA), and the like. The electronic device may be implemented as a portable communication terminal which has a wireless communication function and a pocket size. Further, the electronic device may be a flexible device or a flexible display device.

The electronic device may communicate with an external electronic device, such as a server or the like, or perform an operation through an interworking with the external electronic device. For example, the electronic device may transmit an image photographed by a camera and/or position information detected by a sensor unit to the server through a network. The network may be a mobile or cellular communication network, a Local Area Network (LAN), a Wireless Local Area Network (WLAN), a Wide Area Network (WAN), an Internet, a Small Area Network (SAN) or the like, but is not limited thereto.

FIG. 1 is a perspective illustrating an electronic device 100 according to various embodiments of the present disclosure.

Referring to FIG. 1, an electronic device 100 according to various embodiments of the present disclosure may include a housing 101 having at least one face opened, a window member 101a mounted on the opened face of the housing 101, and an electronic component 115a disposed to face outward on the window member 101a. An opening may be formed in the window member 101a so as to expose the electronic component 115a to the outside.

The housing 101 may be opened in the front face thereof, and may have a power key, a volume key, a storage medium slot, a sound input hole, various connector holes (e.g., a data cable hole or an earphone jack hole) disposed in the side surface thereof. According to one embodiment, the rear face of the housing 101 may be closed. For example, the housing 101 may have a structure in which the side face and the rear face are integrally formed by a single material. In another embodiment, the rear face of the housing 101 is opened, and a separate cover member may be detachably provided thereto. When the rear face of the housing 101 is opened, a storage medium slot, a battery mounting recess, or the like may be disposed on the rear face of the housing 101 and may be concealed by the cover member.

According to various embodiments, the window member 101a may be mounted on an opened face (e.g., the front face) of the housing 101, and a display element (e.g., a display element 313 in FIG. 3) may be incorporated in the inner face of the window member 101a such that a portion of the window member 101a may be used as a screen output region 111. According to one embodiment, the electronic component 115a may be disposed on one side of the screen output region 111, for example, on one side of a region where the display element is disposed. In some embodiments, a sound output hole 113, a proximity sensor and an illuminance sensors 117a and 117b, a camera module 117c, and the like may be disposed around the screen output region 111 of the window member 101a. In another embodiment, around the screen output region 111 of the window member 101a, touch key(s) 115b and 115c may be disposed on the opposite sides of the electronic component 115a. For example, the touch keys 115b and 115c may be used as input devices of a keypad or the like in combination with the electronic component 115c. For example, the electronic component 115a may be utilized as a mechanically operating key (or button).

According to various embodiments, the electronic component 115a may include at least one sensor element, for example, a fingerprint sensor element, an iris scan sensor element, a proximity sensor element, and an illuminance sensor element. In some embodiments, the electronic component 115a may be utilized as a key of the electronic device 100, as mentioned above. For example, the electronic component 115a may be used as a home key for calling the main screen of the electronic device 100. In some embodiments, the electronic component 115a may be utilized as a hot key, in which respective functions assigned according to the operated time, the number of times, and the like are executed. For example, the electronic component 115a itself may be utilized as a biometric sensor, a proximity sensor, an illuminance sensor, or the like, and may be utilized as a mechanically operating key (or button).

Figure 2:
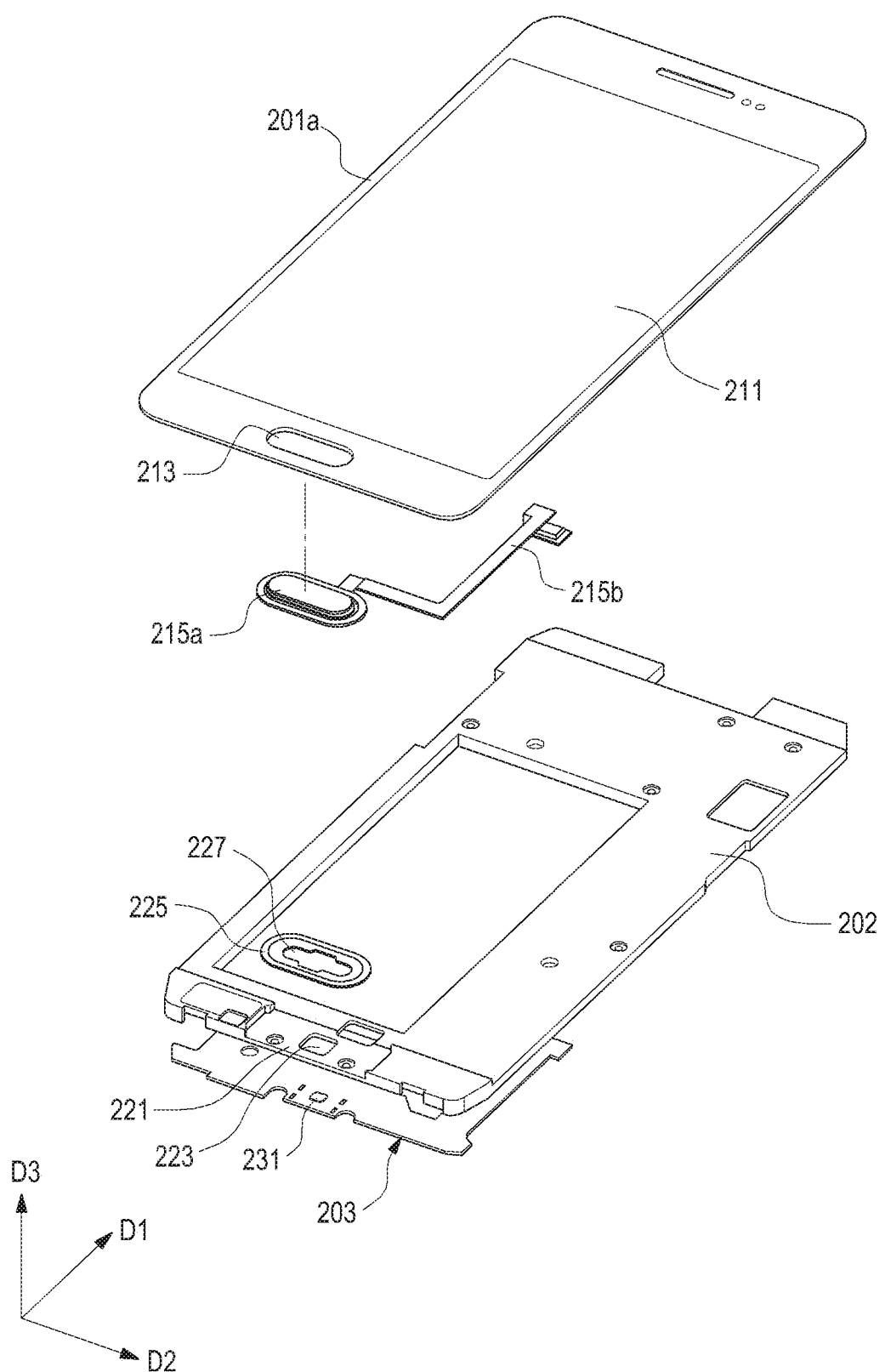
FIG. 2 is an exploded perspective view illustrating a portion of an electronic device according to various embodiments of the present disclosure.

FIG. 2 is an exploded perspective view illustrating a portion of an electronic device according to various embodiments of the present disclosure.

Referring to FIG. 2, the electronic device (e.g., the electronic device 100 in FIG. 1) may include an opening 213 formed on one side of the screen output region 211 of the window member 201a. An electronic component 215a (e.g., the electronic component 115a in FIG. 1) including a sensor element may be disposed in the opening 213 such that at least a portion (e.g., the upper surface) thereof may be exposed to the outside. According to various embodiments, the electronic component 215a may be disposed to be movable back and forth within the opening 213. For example, the electronic component 215a may be utilized as a mechanically operating key while being utilized as a sensor that detects biometric authentication or information on the operating environment of the electronic device.

According to various embodiments, the electronic device may include a coupling member 225 to mount the electronic component 215. For example, the coupling member 225 may be coupled to the inner face of the window member 201a in the state of covering a part (or the entirety) of the lower face of the electronic component 215a. In one embodiment, the coupling member 225 is made of an elastic material, so that the electronic component 215a can be coupled to and supported by the window member 201a in the state in which the electronic component 215a is capable of moving back and forth.

According to one embodiment, the electronic device may include a main circuit board 203, on which integrated circuit chips such as an application processor and a communication module are mounted, and the electronic component 215a may include a flexible printed circuit board 215b. For example, the electronic component 215a may be connected to the main circuit board 203 through the flexible printed circuit board 215b. In some embodiments, the electronic device (e.g., the electronic device 100 in FIG. 1) may include a support member 202 so as to protect a display device (e.g., the display device 313 in FIG. 3) incorporated in the window member 201a. For example, the support member 202 may be disposed between the window member 201a and the main circuit board 203, and is capable of preventing the main circuit board 203 or the integrated circuit chips mounted on the main circuit board 203 from interfering with the display element.

According to various embodiments, the coupling member 225 may be coupled to the support member 202 in the state of being attached to the electronic component 215a. For example, the coupling member 225 may be coupled to one of the window member 201a and the support member 202 or may be coupled to the window member 201a and the support member 202 at the same time. In coupling the coupling member 225 to the window member 201a and/or the support member 202, an adhesive material such as an adhesive or double-sided tape may be used. In one embodiment, when the electronic component 215a is thicker than the window member 201a, the electronic component 215a may partially protrude on the outer face and/or the inner face of the window member 201a. When a portion of the electronic component 215a protrudes on the inner face of the window member 201a, the support member 202 may include an accommodation recess 221 to accommodate a portion of the electronic component 215a.

According to various embodiments, at least one switch element 231 (e.g., a dome switch) may be disposed on the main circuit board 203. The switch element 231 may be disposed to correspond to the electronic component 215a and may be operated in accordance with the back-and-forth movement of the electronic component 215a. For example, an operation hole 223 corresponding to a position where the electronic component 215a is disposed may be disposed on the support member 202, and the electronic component 215a and the switch element 231 may be disposed to at least partially face each other through the operation hole 223. In one embodiment, when the electronic component 215a is disposed in the accommodation recess 221, the opening 223 may be formed through a portion of the accommodation recess 221. When the electronic component 215a is utilized as a mechanically operating key, since the coupling member 225 including a through hole 227 such that a portion of the lower face of the electronic component 251a may disposed to directly face the switch element 231.

In this way, the electronic component 215a according to various embodiments of the present disclosure may be utilized as a mechanically operating key (or a button) on the electronic device while being utilized as a security module for biometric authentication or a sensor for detecting information on the operating environment of the electronic device (e.g., access of an external object or illuminance).

Figure 3:
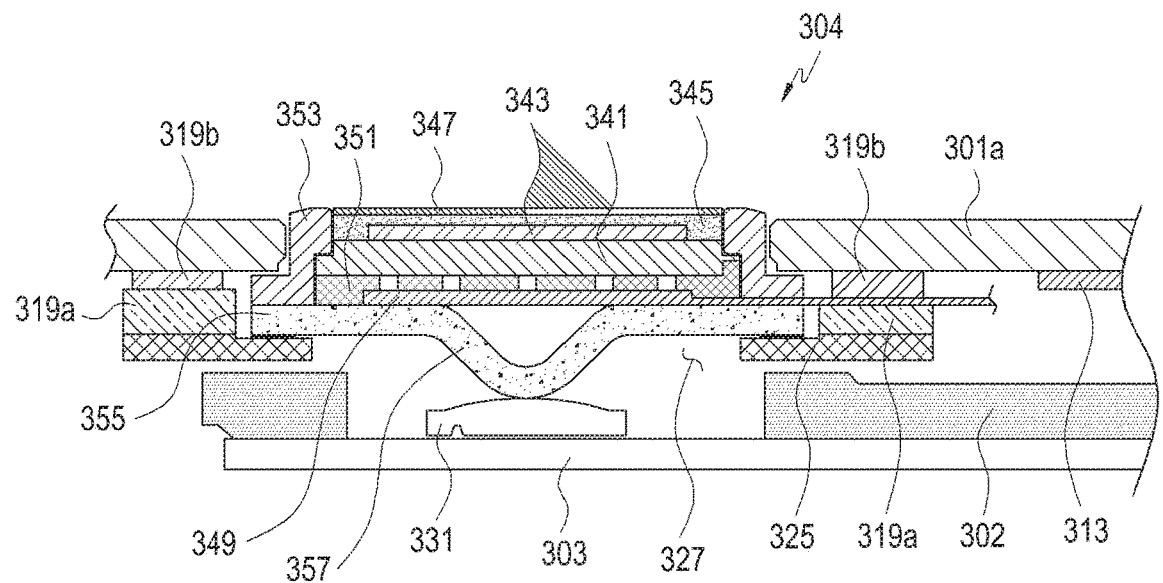
FIG. 3 is a cross-sectional view illustrating the electronic device according to various embodiments of the present disclosure in which a portion of the electronic device is cut away.

FIG. 3 is a cross-sectional view illustrating the electronic device according to various embodiments of the present disclosure in which a portion of the electronic device is cut away.

Referring to FIG. 3, an electronic component 304 may be coupled to the inner face of the window member 301a by a coupling member 325 (e.g., the coupling member 225 in FIG. 2). In some embodiments, the coupling member 325 may be coupled to the inner face of the window member 301a through adhesive members 319a and 319b of, for example, double-sided tape, polar tape, or adhesive. In one embodiment, the coupling member 325 may be coupled to the inner face of the window member 301a in the state of supporting a portion (e.g., an edge) of the lower face of the electronic component 304. A portion of the electronic component 304 may be exposed to the outside through an opening of the window member 301a (e.g., the opening 213 in FIG. 2).

A main circuit board 303 is disposed inside the window member 301a, and a support member 302 may be disposed between the window member 301a and the main circuit board 303. The support member 302 is capable of protecting, for example, the display element 313 disposed on the inner face of the window member 301a, from interference with the main circuit board 303 or the like. On the main circuit board 303, a switch element 331 (e.g., the switch element 231 in FIG. 2) may be disposed to at least partially face the electronic component 304 through an operation hole (e.g., the operation hole 223 in FIG. 2) formed in the support member 302. For example, a through hole 327 is also provided in the coupling member 325, and the switch element 331 may be disposed to face the electronic component 304 through the through hole 327 and the operation hole.

According to various embodiments, the electronic component 304 may include an actuating member 355. For example, the actuating member 355 is mounted on the bottom face of the electronic component 304, and the actuating member 355 may include an actuating protrusion 357 protruding toward the switch element 331. For example, the electronic component 304 is capable of performing back-and-forth movement (e.g., up-and-down movement) on the window member 301a by an external force (e.g., the user's operation), and according to the back-and-forth movement of the electronic component 304, the actuating protrusion 357 is capable of operating the switch element 331, for example, a dome switch.

According to one embodiment, the electronic component 304 may be utilized as a sensor for biometric authentication (e.g., fingerprint recognition, iris recognition, etc.) or detecting information on the operating environment of the electronic device. For example, the electronic component 304 may include at least one sensor element 343 such as a fingerprint sensor element, an iris recognition sensor element, a proximity sensor element, or an illuminance sensor element. The sensor element 343 is mounted on one face of the substrate 341 and may be disposed to face the outside through the opening in the window member 301a when the electronic component 304 is coupled to the window member 301a. In some embodiments, the sensor element 343 may be connected to the main circuit board 303 via a flexible printed circuit board 349 (e.g., the flexible printed circuit board 215b in FIG. 2) coupled to the other face of the substrate 341. According to one embodiment, the flexible printed circuit board 349 may be disposed and extended between the window member 301a and the coupling member 325, for example, between the adhesive members 319a and 319b.

According to various embodiments, the electronic component 304 may include coating layers 345 and 347 to protect the sensor element 343 and to match the appearance of the electronic device. For example, the electronic component 304 may include a first coating layer 345 formed on one face of the substrate 341 so as to surround a part or entirety of the sensor element 343. The first coating layer 345 is capable of isolating and protecting the sensor element 343 from external electromagnetic interference. For example, the first coating layer 345 may include an electromagnetic shielding layer and/or an electromagnetic compatibility coating layer so as to block the influence of external electromagnetic fields and to provide a stable operating environment of the sensor element 343. In one embodiment, the electronic component 304 may further include a second coating layer 347 formed on the first coating layer 345. The second coating layer 347 may include a color layer or a clear coating layer so as to protect the first coating layer 345 and the like from the external environment while providing a decorative effect.

In one embodiment, the electronic component 304 may include a molding portion 351 and/or a case member 353. The molding portion 351 may be formed on at least a portion of the side faces of the substrate 303, the sensor element 343, the first and second coating layers 345 and 347 or between the electronic component 304 and the flexible printed circuit board 349. For example, the molding portion 351 is formed to enclose at least a joint portion between the substrate 341 and the flexible printed circuit board 349, so that the substrate 341 and the flexible printed circuit board 349 can be stably fixed.

According to various embodiments, the case member 353 may have a ring shape or a closed curve shape enclosing the molding portion 351, and a portion of the case member 353 may be positioned on the upper face of the electronic component 304. For example, the case member 353 may be exposed on one face of the substrate 341 and may be located at least around the second coating layer 347. The case member 353 may enhance a decoration effect by partially including a metal material in, for example, a portion exposed to the outside.

Figure 4:
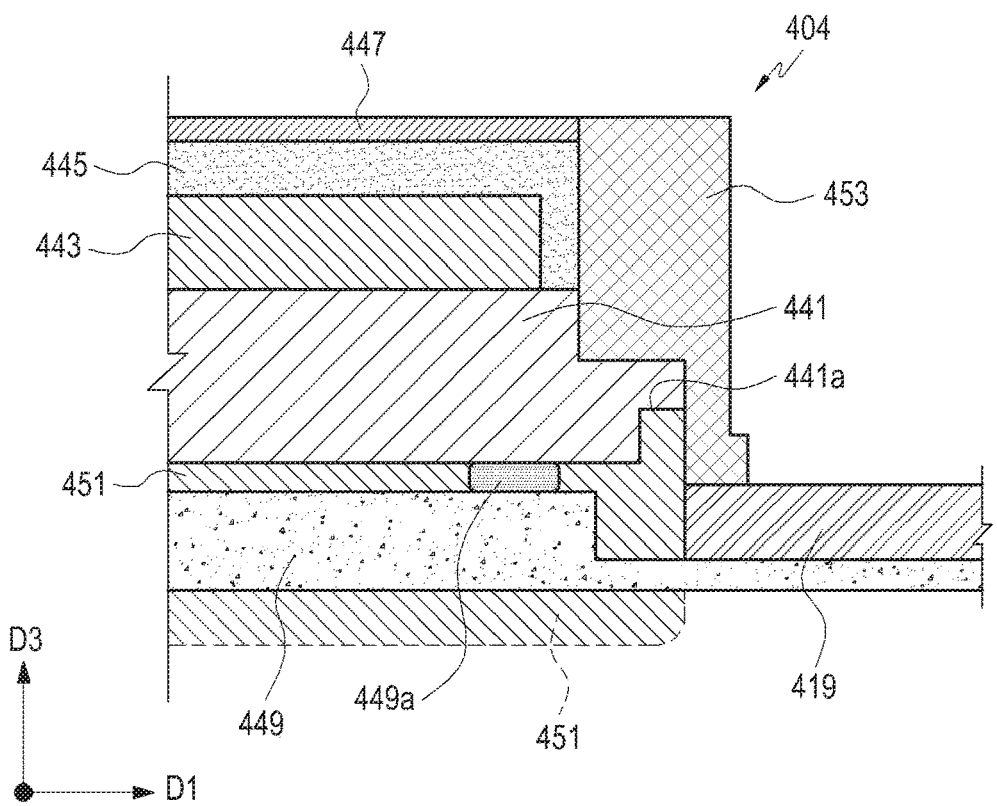
FIG. 4 is a cross-sectional view illustrating an electronic component according to various embodiments of the present disclosure.
Figure 5:
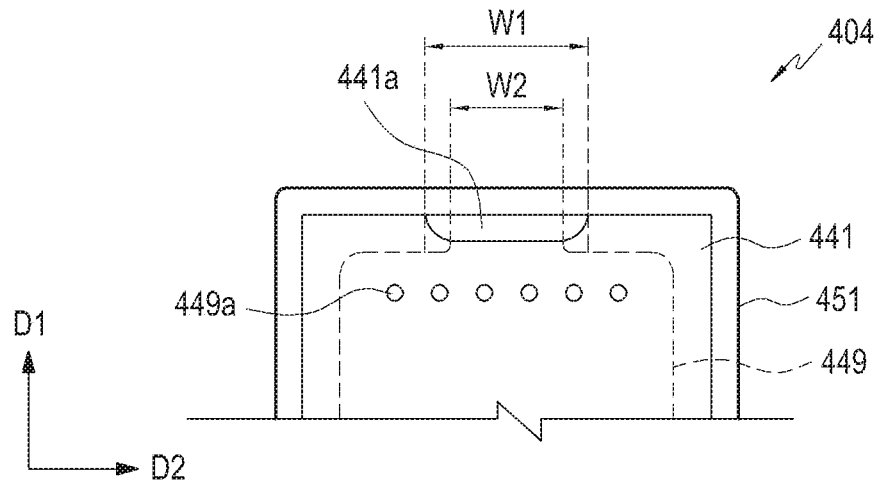
FIG. 5 is a cross-sectional view illustrating an electronic component according to various embodiments of the present disclosure.

FIG. 4 is a cross-sectional view illustrating an electronic component 404 according to various embodiments of the present disclosure. FIG. 5 is a cross-sectional view illustrating the electronic component 404 according to various embodiments of the present disclosure.

Referring to FIG. 4, the electronic component 404 may include a substrate 441, on which a sensor element 443 is mounted, a flexible printed circuit board 449 coupled to the substrate 441, and a recess 441a formed in the substrate 441.

The sensor element 443 may be any one of, for example, a fingerprint sensor element, an iris recognition sensor element, a proximity sensor element, and an illuminance sensor element, and one or more sensor elements 443 may be disposed on one face of the substrate 441. For example, it may be possible to recognize the user's fingerprint and iris through, for example, one electronic component 404.

The flexible printed circuit board 449 may be coupled to the other face of the substrate 441 through a Ball Grid Array (BGA). As will be described below, a plurality of electrode pads may be formed on the flexible printed circuit board 449, and respective solder bumps 449a may be formed on the electrode pads so as to provide a means to be coupled to the substrate 441. In some embodiments, solder paste may be applied to the electrode pads of the flexible printed circuit board 449 so as to provide a means to be coupled to the substrate 441. In other embodiments, a Surface Mounting Technology (SMT) may be utilized in coupling the substrate 441 and the flexible printed circuit board 449 to each other. Since the solder bumps 449a are positioned between the flexible printed circuit board 449 and the substrate 441, the flexible printed circuit board 449 can be coupled to the substrate 441 so as to face the substrate 441 with a predetermined spacing therebetween.

According to various embodiments, the electronic component 404 may include a first coating layer 445 that provides electromagnetic shielding and/or electromagnetic compatibility. The first coating layer 445 may be formed on, for example, one face of the substrate 441 so as to enclose at least the sensor element 443. For example, it is possible to provide an environment where the sensor element 443 is capable of operating stably by isolating the sensor element 443 from the electromagnetic field of the external environment. In one embodiment, the electronic component 404 may include a molding portion 451. For example, at least a portion of the molding portion 451 is formed between the substrate 441 and the flexible printed circuit board 449 so as to seal the space between the substrate 441 and the flexible printed circuit board 449. In another embodiment, the molding portion 451 may be formed to enclose a portion of the flexible printed circuit board 449. For example, of the flexible printed circuit board 449, a portion or region facing the substrate 441 may be at least partially enclosed by another portion of the molding portion 451. In this way, the electronic component 404 according to various embodiments of the present disclosure and/or an electronic device (e.g., the electronic device 100 of FIG. 1) including the electronic component 404 may be formed to enclose a joint portion between the substrate 441 and the flexible printed circuit board 449, so that the substrate 441 and the flexible printed circuit board 449 can be firmly fixed and coupled to each other.

According to one embodiment, the electronic component 404 may further include a case member 453 enclosing at least a portion of the periphery of the molding portion 451. When the case member 453 is coupled to, for example, an electronic device (e.g., the electronic device 100 of FIG. 1), a portion of the case member 453 may be exposed to the outside so as to provide a decorative effect. In another embodiment, the electronic component 404 may further include a second coating layer 447, in which the second coating layer 447 may be formed in a region surrounded by the case member 453 on the upper face of the electronic component 404.

According to various embodiments, the flexible printed circuit board 449 may be provided with an adhesive member (e.g., the adhesive members 319a and 319b in FIG. 3) or a shield member 419. As will be described below, the shield member 419 is capable of preventing the flexible printed circuit board 419 from being damaged in the process of laser processing (laser cutting) for removing a portion of the substrate 441.

As described above, the electronic component 404 may be used as a sensor having a security function such as biometric authentication, or detecting information on the operating environment of the electronic device, and the like, and may be utilized as a mechanically operating key (or button) in some embodiments.

Further referring to FIG. 5, the electronic component 404 may include at least one recess 441a formed in the substrate 441. The recess 441a is formed on the other face of the substrate 441 (e.g., the face opposite the face on which the sensor element 443 is disposed or the face facing the flexible printed circuit board 449) at or adjacent to an edge of the other face. In one embodiment, when the flexible printed circuit board 449 extends to one side of the substrate 441 in a first direction D1, the recess 441a may extend in a second direction D2 intersecting or orthogonal to the first direction D1. The flexible printed circuit board 449 may be disposed to be at least partially correspond to a region where the solder bumps 449a are arranged on the other face of the substrate 441, and may extend to pass through the section where the recess 441a is formed. For example, the recess 441a may extend across the region facing the flexible printed circuit board 449 on the other face of the substrate 441. In some embodiments, the extending length of the recess 441a may be greater than or equal to the width W1 or W2 of the flexible printed circuit board.

According to one embodiment, before being coupled to the electronic device, a portion of the substrate 441 may be removed according to the specifications of the electronic device, for which a laser may be utilized. The laser is capable of forming a cut face of the substrate 441 smoothly (or flatly). For example, by cutting and removing a portion of the substrate 441 using a laser, it is possible to prevent the formation of imperfections (e.g., a burr) on the cut face of the substrate 441. However, when the output of the laser is high in the process of cutting and removing a portion of the substrate 441, the flexible printed circuit board 449 may be damaged by the laser. In order to prevent damage to the flexible printed circuit board 449, the substrate 441 may be partially cut and removed in the state in which the output of the laser is lowered. However, when the output of the laser is lowered, a portion of the substrate 441 may not be completely removed, and imperfections (e.g., a burr) may be formed on the cut face. The imperfections formed on the cut face of the substrate 441 may interfere with the case member 453 and may obstruct assembly of the case member 453. For example, the spacing between the substrate 441 and the flexible printed circuit board 449 is only a few millimeters. Therefore, in removing a portion of the substrate 441, it may be difficult to set the output of the laser so as to smoothly form the cut face of the substrate 441 (not to generate imperfections) without damaging the flexible printed circuit board 449.

In the electronic component 404 according to various embodiments of the present disclosure, it is possible to prevent surface imperfections from being formed and it is also possible to prevent damage to the flexible printed circuit board 449 in the process of cutting and removing a portion of the substrate 441 by forming the recess 441a in the substrate 441 on the face facing the flexible printed circuit board 449. According to one embodiment, the recess 441a may be formed at least in the region facing the flexible printed circuit board 449 along a line to cut a portion of the substrate 441. In the section where the recess 441a is formed, since the thickness of the substrate 441 becomes smaller than that of the other portions, it is possible to secure a flat cut surface free from surface imperfections even if the output of the laser is lowered. Since the output of the laser radiated to cut the section where the recess 441a is formed is lowered, it is possible to prevent the flexible printed circuit board 449 from being damaged.

According to one embodiment, the shield member 419 is disposed in a region corresponding to the line to cut a portion of the substrate 441 so as to block the laser from reaching the flexible printed circuit board 449, whereby it is possible to prevent the flexible printed circuit board 449 from being damaged. In another embodiment, a plurality of recesses 441a may be formed in the substrate 441, and a laser may be radiated along one of the plurality of recesses 441a according to the specifications required for the electronic device. In the specific embodiments illustrated in FIGS. 4 and 5, a configuration is exemplified in which the recess 441a is formed only at the edge of the substrate 441. However, in another embodiment, other recess(es) parallel to the recess 441a may formed in the other face of the substrate 441. For example, when three recesses parallel to each other are formed on the substrate 441 and a laser is radiated along the outermost recess, three recesses may be formed on the other face of the substrate 441 of a completed electronic component. In some embodiments, when three recesses parallel to each other are formed on the substrate 441 and a laser is radiated along the central recess, two recesses may be formed on the other face of the substrate 441 of a completed electronic component. In another embodiment, one of the recesses formed in the other face of the substrate 441 may be located at the edge of the substrate 441.

Figure 6:
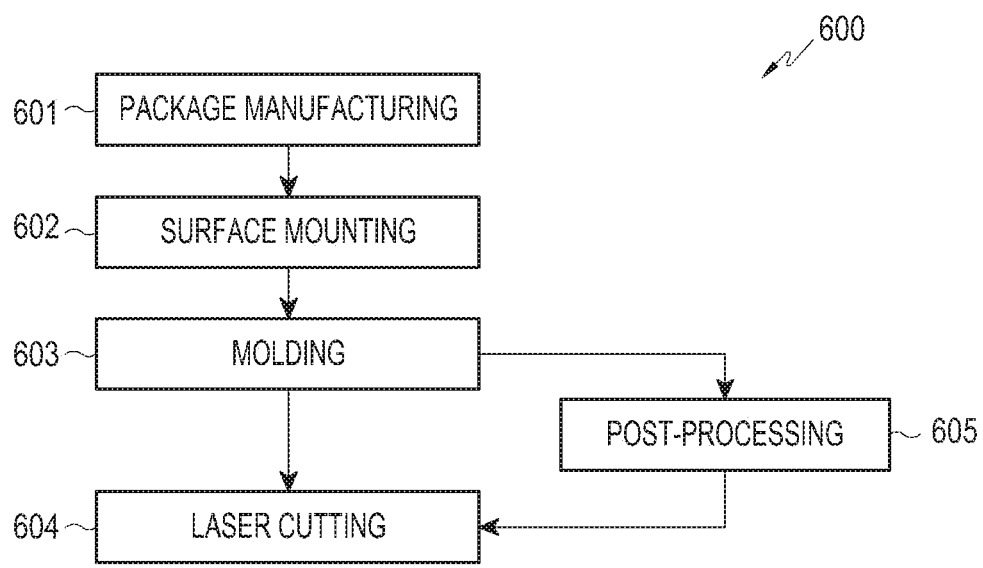
FIG. 6 is a flowchart illustrating a method of manufacturing an electronic component according to various embodiments of the present disclosure.
Figure 7:
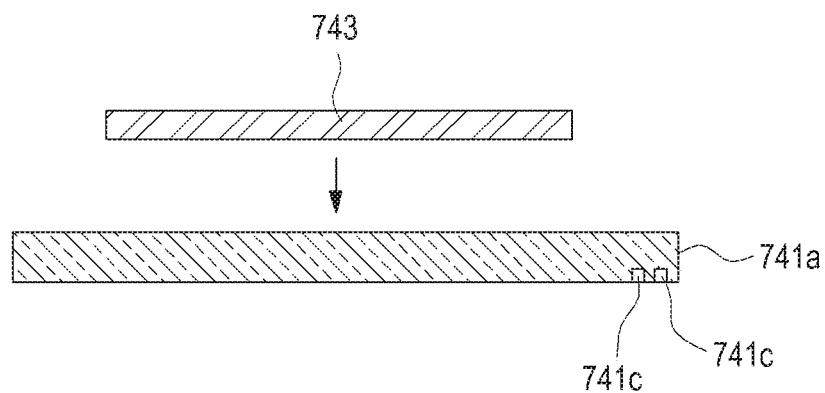
FIGS. 7 to 12 are views each illustrating a process of manufacturing an electronic component according to various embodiments of the present disclosure.
Figure 12:
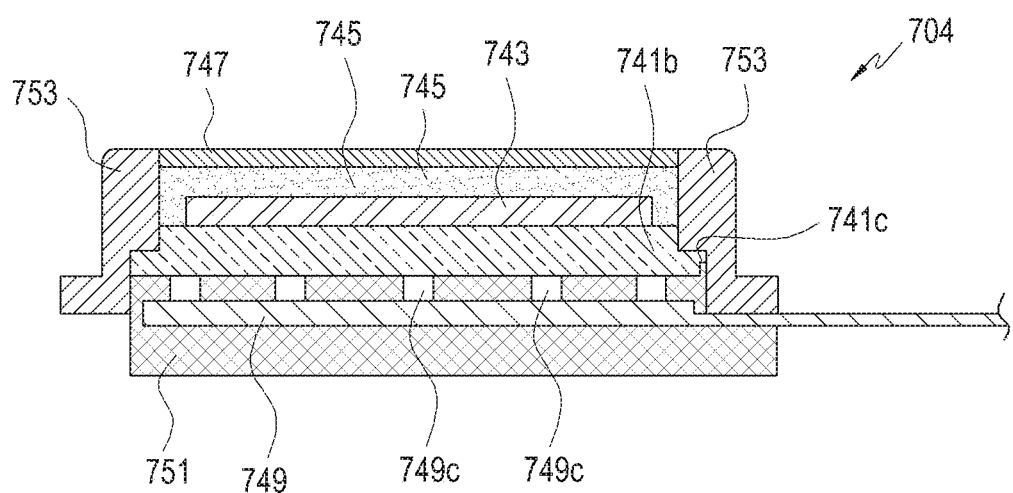

FIG. 6 is a flowchart illustrating an electronic component manufacturing method (600) according to various embodiments of the present disclosure. FIGS. 7 and 12 are views each illustrating a process of manufacturing an electronic component according to various embodiments of the present disclosure.

Referring to FIG. 6, the electronic component manufacturing method (600) according to various embodiments of the present disclosure may include a package manufacturing operation (601), an operation of mounting the package on a flexible printed circuit board (hereinafter, referred to as a "surface mounting operation (602)"), a molding operation (603), and a cutting operation (604), and, in some embodiments, may further include a post-processing operation (605) after the molding operation (603).

Figure 8:
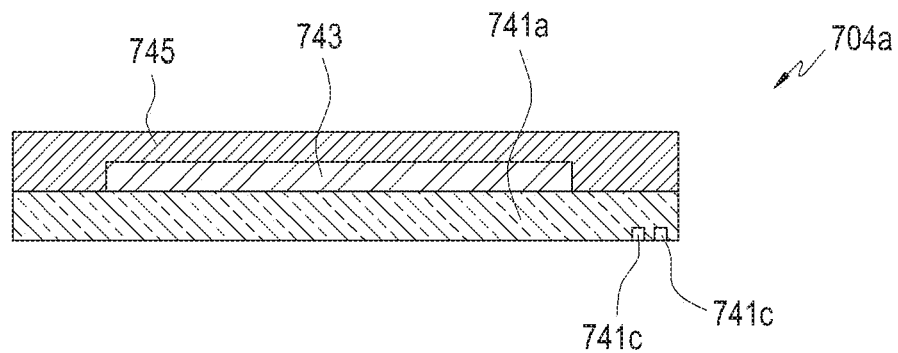

Further referring to FIGS. 7 and 8, the package manufacturing operation (601) may include an operation of disposing a sensor element 743 on a substrate 741a and forming a first coating layer 745. According to one embodiment, the package manufacturing operation (601) may further include an operation of forming at least one recess 741c on the substrate 741a before or after disposing the sensor element 743 and/or before or after forming the first coating layer 745. The recess(es) 741c may be formed on a face opposite the face on which the sensor element 743 is disposed. In some embodiments, the recess(es) 741c may be formed on the other face of the substrate 741a in a region facing the flexible printed circuit board 749 by the surface mounting operation (602).

Figure 9:
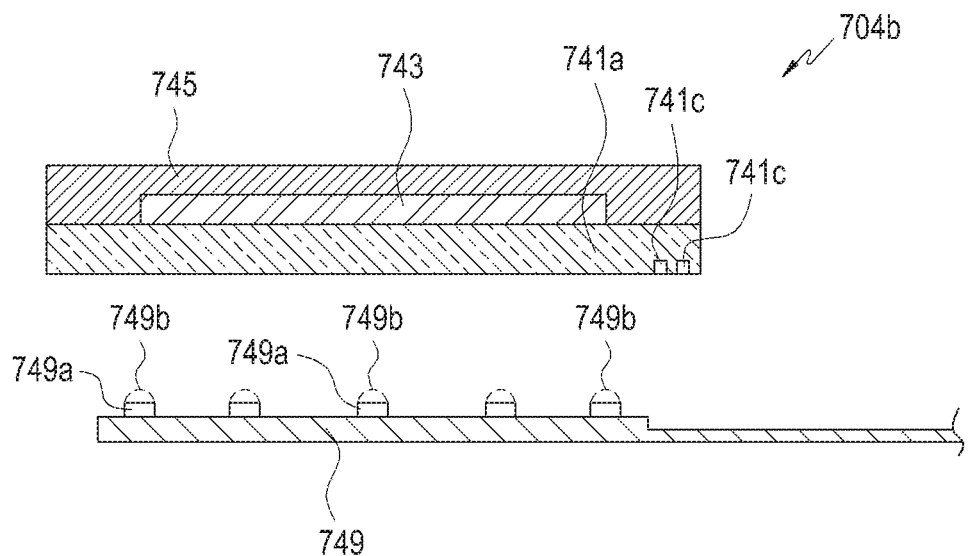

Further referring to FIG. 9, the surface mounting operation (602) is the operation of manufacturing a module 704b by coupling the manufactured package 704a to the flexible printed circuit board 749, in which solder bumps 749b are formed on respective electrode pads 749a of the flexible printed circuit board 749 or solder paste is applied to the electrode pads 749a of the package 704a and the solder bumps 749b or the solder paste are heated, fused, and cured in the state where the package 704a is disposed thereon, whereby the module 704b in which the package 704a and the flexible printed circuit board 749 are coupled can be completed. According to one embodiment, the substrate 741a may be coupled to the flexible printed circuit board 749 through the ball grid array, and a predetermined extent of a spacing or a space may be coupled between the substrate 741a and the flexible printed circuit board 749.

Figure 10:
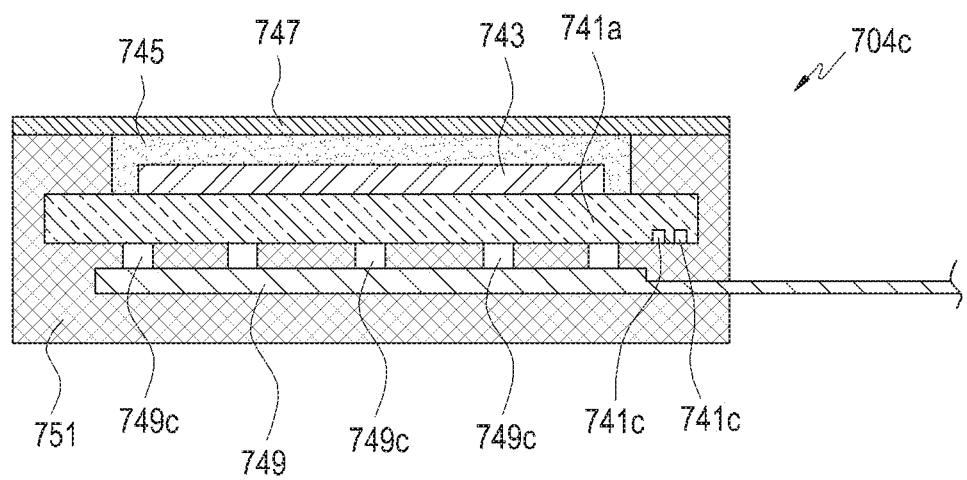

Further referring to FIG. 10, the molding operation (603) is an operation of forming a molding portion 751 around the module 704b with a molding resin, in which it is possible to manufacture a molded module 704c by forming the molding portion 751 on the side face and/or the rear face of the module 704b. According to various embodiments, the molding portion 751 may seal a space formed between the substrate 741a and the flexible printed circuit board 749 by the cured solder bumps 749c, and may be formed to enclose a portion of the flexible printed circuit board 749 positioned on the substrate 741a. The upper face of the module 704b, for example, the first coating layer 745 may be exposed to the outside of the molding portion 751 in the state in which the molding portion 751 is formed. In some embodiments, the plurality of the modules 704b may be arranged and buried in the molding portion 751 at regular intervals. For example, the plurality of the modules 704b may be buried in one molding unit 751, and the molding unit 751 and the like may be cut and machined in an appropriate shape and size so as to conform to the specification and shape of an electronic device to be manufactured, whereby an electronic component may be completed in the form of a single piece. According to another embodiment, the molding operation (603) may further include an operation of forming the second coating layer 747 on the upper face of the molded module 704c (e.g., the first coating layer 745 and/or the upper face of the molding portion 751). For example, the second coating layer 747 may be formed to cover the upper face of the first coating layer 745 and/or the upper face of the molding portion 751 after the molding portion 751 is formed. According to one embodiment, the second coating layer 747 may make the electronic device (e.g., the electronic device 100 in FIG. 1) and the module 704b provided in the electronic device harmonized with each other in appearance.

Figure 11:
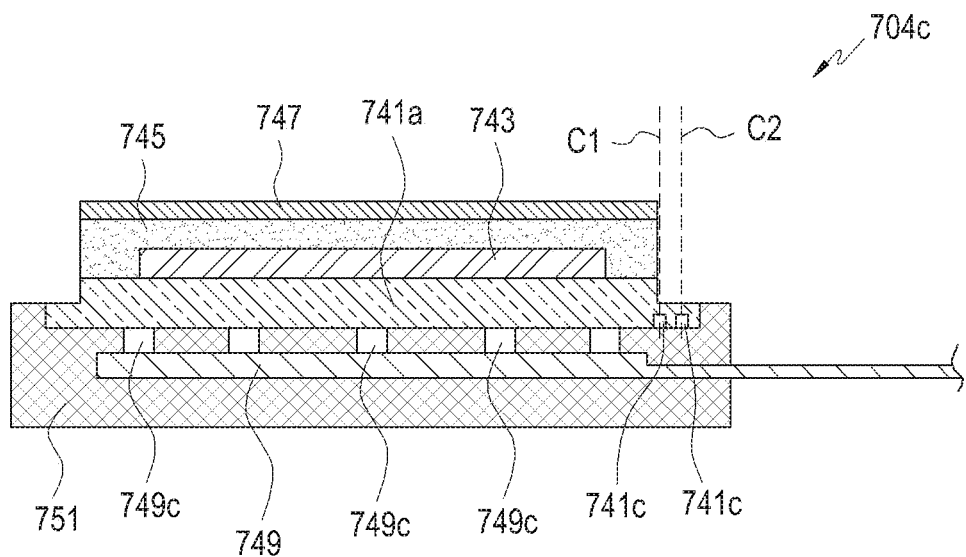

Further referring to FIG. 11, the cutting operation (604) may include an operation of removing a portion of the substrate 714a by cutting the substrate 741a at a predetermined position (e.g., a position indicated by "C1" or "C2") to match the electronic device. The cutting position on the substrate 741a may be one of the positions where the recesses 741c are formed. In some embodiments, only one recess 741c may be formed, and may have a sufficiently large width. For example, although a configuration in which a plurality of the recesses 741c are formed is illustrated in FIG. 11, one recess having a sufficient size (e.g., a width) capable of including a section or region in which the recesses 741c are formed may be formed on the substrate 741a. When a plurality of recesses 741c are formed, the number of recesses formed in the substrate 741a before the cutting operation (604) and the number of recesses formed in the substrate after the cutting operation (604) (e.g., the substrate 741b in FIG. 12) may be different.

As described above, the electronic components according to various embodiments of the present disclosure may be manufactured in a large quantity according to predetermined standards in the process of manufacturing the electronic components themselves, and may then be processed into an appropriate size to match the specification, shape, or the like of an electronic device in the process of being mounted in the electronic device. For example, even if the design or the like of an electronic device is changed, the electronic components may be processed into a suitable shape and size in the cutting operation so as to correspond to the changed design of the electronic device. Therefore, it is possible to improve the flexibility of design of an electronic device while contributing to the reduction of manufacturing costs according to mass production.

In some embodiments, the recess 741c may be formed to extend across the region facing the flexible printed circuit board 749 on the other face of the substrate 741a. For example, when cutting the region facing the flexible printed circuit board 749 (e.g., the region or section where the recess 741c is formed) is cut in the operation of cutting the substrate 741a using a laser, it is possible to prevent surface imperfections (e.g., a burr) from being generated and formed on the cut face of the substrate 741a even if the output of the laser is lowered. In another embodiment, when the region facing the flexible printed circuit board 749 (e.g., the region or section where the recess 741c is formed) is cut, it is possible to prevent the flexible printed circuit board 749 from being damaged by a laser by lowering the output of the laser.

According to various embodiments, the post-processing operation (605) may be performed prior to the cutting operation (604), for example. When cutting the substrate 741a, a laser may also be radiated to the molding portion 751 and/or the second coating layer 747. Since the molding portion 751 and/or the second coating layer 747 are formed of a synthetic resin, the molding portion 751 and/or the second coating layer 747 may be deformed or discolored by heat when exposed to a laser. In the post-processing operation (605), it is possible to prevent the molding portion 751 and/or the second coating layer 747 from being deformed or discolored by the cutting operation (604) (e.g., by radiation of a laser) by removing at least the portion to which the laser is to be radiated by grinding or cutting the molding portion 751 and/or the second coating layer 747 on one face of the substrate 741a (the face on which the sensor element 743 is disposed).

Referring to FIG. 12, the electronic component 704 completed by the cutting operation (604) may be mounted on the electronic device as it is, but the case member 753 may be coupled to protect the molded module 704c. Although not described in the present embodiment, when the electronic component 704 is utilized as a mechanically operating key, the electronic component 704 may further include an actuating member (e.g., the actuating member 355 in FIG. 3) provided on the bottom face thereof.

As described above, according to various embodiments of the present disclosure, an electronic device may include:
  a substrate having a sensor element mounted on one face thereof;
  a flexible printed circuit board coupled to face a remaining face of the substrate and extending to one side of the substrate in a first direction; and
  at least one recess formed at an edge of the remaining face of the substrate,
  in which the recess may be located at least in a region facing the flexible printed circuit board on the remaining face of the substrate, and may extend in a second direction intersecting the first direction.

According to various embodiments, the recess may extend across the region facing the flexible printed circuit board on the remaining face of the substrate.

According to various embodiments, at least one end of the recess may extend out of the region facing the flexible printed circuit board on the remaining face of the substrate.

According to various embodiments, the sensor element may include at least one of a fingerprint sensor element, an iris scan sensor element, a proximity sensor element, and an illuminance sensor element.

According to various embodiments, the electronic component may further include a first coating layer coated on the one face of the substrate so as to enclose at least the sensor element.

According to various embodiments, the first coating layer may include an ElectroMagnetic Compatibility (EMC) coating layer.

According to various embodiments, the electronic component may further include a second coating layer formed on the first coating layer.

According to various embodiments, the electronic component may further include a molding portion provided to enclose at least a periphery of the substrate.

According to various embodiments, the flexible printed circuit board may be coupled to the remaining face of the substrate via a Ball Grid Array (BGA), and a portion of the molding portion may seal a space between the substrate and the flexible printed circuit board.

According to various embodiments, the molding portion may be formed to enclose at least a portion of the flexible printed circuit board in the periphery of the substrate and the region facing the substrate.

According to various embodiments, the electronic component may further include a case member provided to enclose at least the periphery of the substrate, and the case member may be exposed to the one face of the substrate.

An electronic device according to various embodiments of the present disclosure may include an electronic component as described above.

According to various embodiments, the electronic device may further include
  a housing having at least one opened face,
  a window member mounted on the opened face of the housing, and
  an opening formed in the window member.

The sensor element may be disposed to face an outside of the window member through the opening.

According to various embodiments, the electronic device may further include a display element disposed on an inner face of the window member,
  in which the opening may be formed at a side of a region where the display element is disposed.

According to various embodiments, the electronic device may further include a switch element disposed inside the housing,
  in which at least a portion of the electronic component may be disposed to at least partially face the switch element.

According to various embodiments, the electronic component may perform a back-and-forth movement on the housing so as to operate the switch element.

According to various embodiments, the electronic device may further include an actuating member mounted on a bottom face of the electronic component and disposed to face the switch element,
  in which as the electronic component performs the back-and-forth movement on the housing, the actuating member may operate the switch element.

According to various embodiments, the switch element may include a dome switch mounted on a circuit board.

According to various embodiments, the actuating member may further include an actuating protrusion protruding from one face thereof toward the switch element.

According to various embodiments, the electronic device may further include:
  an actuating member mounted on a bottom face of the electronic component and disposed to face the switch element; and
  an actuating protrusion protruding from one face of the actuating member toward the switch element,
  in which the switch element may include a dome switch mounted on a circuit board, and
  as the electronic component performs a back-and-forth movement on the housing, the actuating protrusion may operate the switch element.

While the present disclosure has been shown and described with reference to certain embodiments thereof, it will be understood by those skilled in the art that various changes in form and details may be made therein without departing from the spirit and scope of the present disclosure as defined by the appended claims.

The invention claimed is:

1. An electronic component comprising:
   a substrate having a sensor element mounted on one face thereof;
   a flexible printed circuit board coupled to face a remaining face of the substrate and extending to one side of the substrate in a first direction; and
   at least one recess formed at an edge of the remaining face of the substrate,
   wherein the recess is located at least in a region facing the flexible printed circuit board on the remaining face of the substrate and extends in a second direction intersecting the first direction.

2. The electronic component of claim 1, wherein the recess extends across the region facing the flexible printed circuit board on the remaining face of the substrate.

3. The electronic component of claim 1, further comprising:
   at least one coating layer coated on the one face of the substrate to enclose at least the sensor element.

4. The electronic component of claim 1, further comprising:
   a molding portion provided to enclose at least a periphery of the substrate.

5. The electronic component of claim 4, wherein the flexible printed circuit board is coupled to the remaining face of the substrate through a Ball Grid Array (BGA), and
   a portion of the molding portion seals a space between the substrate and the flexible printed circuit board.

6. The electronic component of claim 4, wherein the molding portion is formed to enclose the periphery of the substrate and to enclose at least a portion of the flexible printed circuit board in the region facing the substrate.

7. The electronic component of claim 1, further comprising
   a case member provided to enclose at least a periphery of the substrate and exposed to one face of the substrate.

8. An electronic device comprising:
   an electronic component, wherein the electronic component comprises:
   a substrate having a sensor element mounted on one face thereof;
   a flexible printed circuit board coupled to face a remaining face of the substrate and extending to one side of the substrate in a first direction; and
   at least one recess formed at an edge of the remaining face of the substrate,
   wherein the recess is located at least in a region facing the flexible printed circuit board on the remaining face of the substrate and extends in a second direction intersecting the first direction.

9. The electronic device of claim 8, further comprising:
   a housing having at least one opened face;
   a window member mounted on the opened face of the housing; and
   an opening formed in the window member,
   wherein the sensor element is disposed to face an outside of the window member through the opening.

10. The electronic device of claim 9, further comprising:
    a display element disposed on an inner face of the window member,
    wherein the opening is formed at a side of a region where the display element is disposed.

11. The electronic device of claim 9, further comprising:
    a switch element disposed inside the housing,
    wherein at least a portion of the electronic component is disposed to face the switch element.

12. The electronic device of claim 11, wherein the electronic component performs a back-and-forth movement on the housing so as to operate the switch element.

13. The electronic device of claim 11, further comprising:
    an actuating member mounted on a bottom face of the electronic component and disposed to face the switch element,
    wherein as the electronic component performs the back-and-forth movement on the housing, the actuating member operates the switch element.

14. The electronic device of claim 13, wherein the switch element includes a dome switch mounted on a circuit board.

15. The electronic device of claim 13, further comprising:
    an actuating protrusion protruding from one face of the actuating member toward the switch element.

* * * * *